US008273386B2

(12) United States Patent
Maca et al.

(10) Patent No.: US 8,273,386 B2
(45) Date of Patent: Sep. 25, 2012

(54) **USE OF HOP ACIDS IN FRUIT JUICES, FRUIT JUICE CONCENTRATES AND OTHER BEVERAGES TO INHIBIT *ALICYCLOBACILLUS* BACTERIA**

(75) Inventors: Henry William Maca, Grafton, WI (US); Michael C. Barney, Elm Grove, WI (US); David S. Ryder, Mequon, WI (US)

(73) Assignee: MillerCoors LLC, Wilmington, DE (US)

( * ) Notice: Subject to any disclaimer, the term of this patent is extended or adjusted under 35 U.S.C. 154(b) by 176 days.

(21) Appl. No.: 12/858,927

(22) Filed: Aug. 18, 2010

(65) Prior Publication Data

US 2010/0310741 A1  Dec. 9, 2010

Related U.S. Application Data

(62) Division of application No. 11/664,658, filed as application No. PCT/US2005/035043 on Sep. 30, 2005, now Pat. No. 7,803,410.

(60) Provisional application No. 60/615,833, filed on Oct. 4, 2004.

(51) Int. Cl.
  *A01N 65/00* (2009.01)
(52) U.S. Cl. ........................................ 424/725
(58) Field of Classification Search ........................ None
  See application file for complete search history.

(56) References Cited

U.S. PATENT DOCUMENTS

| 4,644,084 | A | 2/1987 | Cowles et al. |
| 5,286,506 | A | 2/1994 | Millis et al. |
| 5,370,863 | A | 12/1994 | Barney et al. |
| 5,455,038 | A | 10/1995 | Barney et al. |
| 6,251,461 | B1 | 6/2001 | Johnson et al. |
| 6,329,011 | B1 | 12/2001 | Oita |
| 6,451,365 | B1 | 9/2002 | King et al. |
| 6,824,801 | B2 | 11/2004 | Yajima et al. |
| 2004/0131709 | A1 | 7/2004 | Berdahl et al. |
| 2004/0175480 | A1 | 9/2004 | Seman et al. |

FOREIGN PATENT DOCUMENTS

| LT | 1992-151 | 12/1992 |
| LT | 1992-160 | 12/1992 |
| LT | 1997-9700095 | 5/1997 |
| SU | 1986-4142237 | 7/1986 |
| SU | 1535518 | 1/1990 |

OTHER PUBLICATIONS

PCT International Search Report and Written Opinion, PCT/US05/35043, May 4, 2006.
Ivanova, T. N., et al., Pishchevaya Promyshlennost (7): p. 60, 2002, CAB Abstract.
PCT International Preliminary Report on Patentability, PCT/US05/35043, Aug. 22, 2006.
Conway, W. S., et al., Survival and Growth of *Listeria monocylogenes* on Fresh-Cut Apple Slices and Its Interaction with *Glomerella cingulata* and *Penicillium expansum*, Plant Disease, 2000, vol. 84, No. 2, pp. 177-181.
Lee, S., et al., Inhibitory Effects of High Pressure and Heat on *Alicyclobacillus acidoterrestris* Spores in Apple Juice, 2002, Appl. Environ. Microbiol., vol. 68, No. 8, pp. 4158-4161.
Supplementary Partial European Search Report, Application No. 05800020.9, Mar. 15, 2010.
Database Biosis [Online] Biosciences Information Service, Philadelphia, PA, US; Jan. 2004, Srinivasan Vanita et al., "Contributions to the antimicrobial spectrum of hop constituents" Database accession No. PREV200500209056; and Economic Botany, vol. 58, No. Suppl. S, Jan. 2004, pp. S230-S238, ISSN: 0013-0001.
United States Patent and Trademark Office, Office Action Summary and Detailed Action, U.S. Appl. No. 11/664,658, Oct. 2, 2009.
United States Patent and Trademark Office, Office Action Summary and Detailed Action, U.S. Appl. No. 11/664,658, Dec. 21, 2009.

*Primary Examiner* — Michael Meller
(74) *Attorney, Agent, or Firm* — Quarles & Brady LLP

(57) ABSTRACT

An antimicrobial agent including hop acids is disclosed that inhibits the growth of acid-resistant and heat-resistant bacteria such as *Alicyclobacillus acidoterrestris* and *Alicyclobacillus acidocaldarius* in a medium such as fruit juice.

5 Claims, No Drawings

USE OF HOP ACIDS IN FRUIT JUICES, FRUIT JUICE CONCENTRATES AND OTHER BEVERAGES TO INHIBIT *ALICYCLOBACILLUS* BACTERIA

CROSS-REFERENCES TO RELATED APPLICATIONS

This application is a divisional application of U.S. patent application Ser. No. 11/664,658 filed Nov. 29, 2007, now U.S. Pat. No. 7,803,410 which is a 371 of PCT/US05/35043 filed Sep. 30, 2005, which claims priority from U.S. Provisional Patent Application No. 60/615,833 filed Oct. 4, 2004.

STATEMENT REGARDING FEDERALLY SPONSORED RESEARCH

Not Applicable.

BACKGROUND OF THE INVENTION

1. Field of the Invention

The present invention relates to an antimicrobial agent against acid-resistant and heat-resistant bacteria, and more specifically, to an antimicrobial agent including hop acids which inhibits the growth of acid-resistant and heat-resistant bacteria such as *Alicyclobacillus acidoterrestris* and *Alicyclobacillus acidocaldarius*.

2. Description of the Related Art

*Alicyclobacillus acidoterrestris* and *Alicyclobacillus acidocaldarius* are acid-resistant and heat-resistant bacteria that cause the spoilage of fruit juice. One of the characteristics of such spoilage is the production of phenolic compounds that affect the taste of the fruit juice as well as clouding of the fruit juice. Because *Alicyclobacillus acidoterrestris* and *Alicyclobacillus acidocaldarius* are acid-resistant and heat-resistant, conventional techniques for bacteria control such as pasteurization and pH reduction are not completely effective in destroying these bacteria. For example, the spores of these bacteria possess resistance against the normally employed pasteurization method for fruit juice. As a result, hot sterile fill and severe pasteurization methods have been used in an effort to destroy these bacteria. Unfortunately, these methods may alter the true to type character of the fruit juice due to the severe heat.

In order to suppress the growth of *Alicyclobacillus acidoterrestris* and *Alicyclobacillus acidocaldarius* in fruit juice, it is reported in U.S. Pat. No. 6,329,011 that nisin, which is a peptide derived from lactic acid bacterium, may be added to fruit juice. This patent also proposes using thionins, which are peptides derived from wheat and barley, to suppress the growth of *Alicyclobacillus acidoterrestris* and *Alicyclobacillus acidocaldarius* in fruit juice.

Even though these known methods for suppressing the growth of *Alicyclobacillus acidoterrestris* and *Alicyclobacillus acidocaldarius* in fruit juice are available, there is still a need for alternative methods for suppressing the growth of *Alicyclobacillus acidoterrestris* and *Alicyclobacillus acidocaldarius* in fruit juice. It would be desirable if such methods would avoid severe heat treatment of the fruit juice so that the natural flavor of the fruit juice is not degraded.

SUMMARY OF THE INVENTION

The present invention provides an antimicrobial agent including a hop acid wherein the antimicrobial agent exhibits growth-inhibitory activity against *Alicyclobacillus acidoterrestris* and *Alicyclobacillus acidocaldarius*, which have acid-resistance and heat-resistance and cause spoilage of fruit juice.

These and other features, aspects, and advantages of the present invention will become better understood upon consideration of the following detailed description and appended claims.

DETAILED DESCRIPTION OF THE INVENTION

The present invention comprises incorporating a safe and effective amount of an antimicrobial agent including a hop acid into a medium to inhibit *Alicyclobacillus* growth. In a preferred embodiment, the hop acid is selected from tetrahydroisohumulone, hexahydrocolupulone, colupulone, and mixtures thereof and the salts thereof. "Safe and effective amount" as used herein means an amount of the antimicrobial agent which is enough to provide the desired growth inhibition, but not so high as to cause undesirable other properties, such as an unacceptable taste. The safe and effective amount will vary with the particular antimicrobial agent chosen, and the taste or flavoring of the particular food to which the antimicrobial agent is to be added. An "effective amount" as used herein means an amount of the antimicrobial agent which is enough to provide the desired growth inhibition. The term "medium" as used herein is intended to include, among other things, both solid and liquid foods.

In one embodiment, the medium is a fruit juice selected from the group consisting of apple, orange, pineapple, cherry, grape, grapefruit, lemon, melon, strawberry, cherry, lemon-lime, mango, papaya, cranapple, fruit punch, peach, guava, tangerine, apricot, cranberry, and mixtures thereof. The term "fruit juice" also includes a fruit juice concentrate, which may be in solid form.

The alpha-acids contained in hops are commonly known as humulone, cohumulone and adhumulone, while the beta-acids contained in hops are commonly known as lupulone, colupulone and adlupulone. These hop acids may be extracted from hops using well known methods. These hop acids are effective in inhibiting *Alicyclobacillus* when used in concentrations of 50 ppm or greater in a solid or liquid medium.

The term "tetrahydroisohumulone" as used herein includes tetrahydroisohumulone, tetrahydroisoadhumulone, tetrahydroisocohumulone, and mixtures thereof. These chemically modified derivatives of hops acids are commercially available or can be prepared, for example, by use of the method of U.S. Pat. No. 4,644,084. The tetrahydroisohumulone is effective in inhibiting *Alicyclobacillus* when used in concentrations of 3 ppm or greater in a solid or liquid medium.

The hexahydrocolupulone is a known compound which can be made by the chemical hydrogenation of colupulone with platinum (IV) oxide as the catalyst as described by J. F. Carson, *J. Am. Chem. Soc.*, 73 (1951) p. 1850. The hexahydrocolupulone is effective in inhibiting *Alicyclobacillus* when used in concentrations of 0.05 ppm or greater in a solid or liquid medium.

Therefore, the invention provides a method of inhibiting the growth of *Alicyclobacillus* in a medium including *Alicyclobacillus*. In the method, an effective amount of a hop acid is added to a medium including *Alicyclobacillus* to inhibit the growth of *Alicyclobacillus* in the medium. Preferably, the method inhibits the growth of *Alicyclobacillus acidoterrestris* and/or *Alicyclobacillus acidocaldarius*. The medium can be, among other things, a liquid or solid food, and in one application of the invention, the medium is a fruit juice.

In one version of the invention, the hop acid is selected from the group consisting of tetrahydroisohumulone, hexahydrocolupulone, colupulone, and mixtures thereof and the salts thereof. When the hop acid is tetrahydroisohumulone, the hop acid is preferably present in the medium in an amount of 3 ppm or greater. The upper limit for the tetrahydroisohumulone is a ppm value at which undesirable properties occur, such as an unacceptable taste. When the hop acid is hexahydrocolupulone, the hop acid is preferably present in the medium in an amount of 0.05 ppm or greater. The upper limit for the hexahydrocolupulone is a ppm value at which undesirable properties occur, such as an unacceptable taste. When the hop acid is colupulone, the hop acid is preferably present in the medium in an amount of 50 ppm or greater. The upper limit for the colupulone is a ppm value at which undesirable properties occur, such as an unacceptable taste.

The invention also provides a food product including a fruit juice and a hop acid. In one version of the food product, the hop acid is selected from the group consisting of tetrahydroisohumulone, hexahydrocolupulone, colupulone, and mixtures thereof and the salts thereof. When the hop acid is tetrahydroisohumulone, the hop acid is preferably present in the food product in an amount of 3 ppm or greater. The upper limit for the tetrahydroisohumulone is a ppm value at which undesirable properties occur, such as an unacceptable taste. When the hop acid is hexahydrocolupulone, the hop acid is preferably present in the food product in an amount of 0.05 ppm or greater. The upper limit for the hexahydrocolupulone is a ppm value at which undesirable properties occur, such as an unacceptable taste. When the hop acid is colupulone, the hop acid is preferably present in the food product in an amount of 50 ppm or greater. The upper limit for the colupulone is a ppm value at which undesirable properties occur, such as an unacceptable taste.

The fruit juice may be selected from the group consisting of apple, orange, pineapple, cherry, grape, grapefruit, lemon, melon, strawberry, cherry, lemon-lime, mango, papaya, cranapple, fruit punch, peach, guava, tangerine, apricot, cranberry, and mixtures thereof. In one example, the fruit juice is apple juice. The food product may include fruit juice at different percentages by volume. For example, the food product may include at least 10% by volume of fruit juice, or at least 25% by volume of fruit juice, or at least 50% by volume of fruit juice, or at least 75% by volume of fruit juice, or at least 90% by volume of fruit juice. In one form, the food product consists essentially of fruit juice, water and the hop acid.

The invention also provides a method for retarding spoilage of a fruit juice. In the method, a safe and effective amount of a hop acid is added to the fruit juice to retard spoilage of the fruit juice, particularly where the fruit juice includes an acid-resistant or heat-resistant bacterium, such as *Alicyclobacillus*.

The hop acid may be selected from the group consisting of tetrahydroisohumulone, hexahydrocolupulone, colupulone, and mixtures thereof and the salts thereof. When the hop acid is tetrahydroisohumulone, the hop acid is preferably present in the fruit juice in an amount of 3 ppm or greater. The upper limit for the tetrahydroisohumulone is a ppm value at which undesirable properties occur, such as an unacceptable taste. When the hop acid is hexahydrocolupulone, the hop acid is preferably present in the fruit juice in an amount of 0.05 ppm or greater. The upper limit for the hexahydrocolupulone is a ppm value at which undesirable properties occur, such as an unacceptable taste. When the hop acid is colupulone, the hop acid is preferably present in the fruit juice in an amount of 50 ppm or greater. The upper limit for the colupulone is a ppm value at which undesirable properties occur, such as an unacceptable taste.

The method retards spoilage of a fruit juice such as juices from apples, oranges, pineapples, cherries, grapes, grapefruit, lemons, melons, strawberries, cherries, limes, mangos, papayas, cranberries, mixed fruit, peaches, guavas, tangerines, apricots, and mixtures thereof. In one example, the method retards spoilage of apple juice.

EXAMPLES

The following Examples have been presented in order to further illustrate the invention and are not intended to limit the invention in any way.

Example 1

Minimal Inhibitory Concentration (MIC) Assay

The basic assay was performed by serially diluting the inhibitors using a two-fold dilution series in a nutrient broth. The dilutions provided inhibitor concentrations in the range of 0.025 ppm to 100 ppm. The nutrient broth used was the American Type Culture Collection *Bacillus* Agar Medium (BAM) (at pH 4.0 and at 45° C.) for the *Alicyclobacillus acidoterrestris*. All dilution series were inoculated with approximately 10,000 bacteria per 5 ml. broth tube of freshly cultured (using the same medium) cells per 5 ml. of test assay broth. In each assay, an inoculated sample of the broth without any inhibitor addition was used as a control. Growth was evaluated by visually assessing and scoring the development of turbidity in the broth after 72 hours.

The results of the studies are summarized in Table 1 which gives the data from testing the effectiveness of the tetrahydroisohumulone, hexahydrocolupulone and colupulone in inhibiting *Alicyclobacillus acidoterrestris*. As the data show, tetrahydroisohumulone inhibited the *Alicyclobacillus acidoterrestris* test strain at a concentration at or above 25 ppm. Hexahydrocolupulone inhibited the *Alicyclobacillus acidoterrestris* test strain at or above 50 ppm. Colupulone inhibited the *Alicyclobacillus acidoterrestris* test strain at or above 50 ppm.

TABLE 1

| | MIC's of *Alicyclobacillus acidoterrestris* with Hop Acids | | |
|---|---|---|---|
| Concentration | Tetrahydroisohumulone Growth in BAM at pH 4.0 at 45° C. | Hexahydrocolupulone Growth in BAM at pH 4.0 at 45° C. | Colupulone Growth in BAM at pH 4.0 at 45° C. |
| 100 ppm | No growth | No growth | No growth |
| 50 pm | No growth | No growth | No growth |
| 25 ppm | No growth | ++++ growth | ++++ growth |
| 12.5 ppm | ++++ growth | ++++ growth | ++++ growth |
| 6.25 ppm | ++++ growth | ++++ growth | ++++ growth |
| 3.125 ppm | ++++ growth | ++++ growth | ++++ growth |

TABLE 1-continued

MIC's of *Alicyclobacillus acidoterrestris* with Hop Acids

| Concentration | Tetrahydroisohumulone Growth in BAM at pH 4.0 at 45° C. | Hexahydrocolupulone Growth in BAM at pH 4.0 at 45° C. | Colupulone Growth in BAM at pH 4.0 at 45° C. |
|---|---|---|---|
| 1.6 ppm | ++++ growth | ++++ growth | ++++ growth |
| 0.8 ppm | ++++ growth | ++++ growth | ++++ growth |
| 0.4 ppm | ++++ growth | ++++ growth | ++++ growth |
| 0.2 ppm | ++++ growth | ++++ growth | ++++ growth |
| 0.1 ppm | ++++ growth | ++++ growth | ++++ growth |
| 0.05 ppm | ++++ growth | ++++ growth | ++++ growth |
| 0.025 ppm | ++++ growth | ++++ growth | ++++ growth |
| 0 ppm Control | ++++ growth | ++++ growth | ++++ growth |

Example 2

Minimal Inhibitory Concentration (MIC) Assay

The basic assay was performed by serially diluting the inhibitors using a two-fold dilution series in a nutrient broth. The dilutions provided inhibitor concentrations in the range of 0.025 ppm to 100 ppm. The nutrient broth used was trypticase soy broth (TSB) (at pH 7.0) for the *Alicyclobacillus acidocaldarius*. All dilution series were inoculated with approximately 10,000 bacteria per 5 ml. of broth using freshly cultured (using the same medium) cells per 5 ml. of test assay broth. In each assay, an inoculated sample of the broth without any inhibitor addition was used as a control. Growth was evaluated by visually assessing and scoring the development of turbidity in the broth after 48 hours.

The results of the studies are summarized in Table 2 which gives the data from testing the effectiveness of the tetrahydroisohumulone and hexahydrocolupulone in inhibiting *Alicyclobacillus acidocaldarius*. As the data show tetrahydroisohumulone inhibited the *Alicyclobacillus acidocaldarius* test strain at a concentration at or above 3.125 ppm. Hexahydrocolupulone inhibited the *Alicyclobacillus acidocaldarius* test strain at or above 0.05 ppm.

TABLE 2

MIC's of *Alicyclobacillus acidocaldarius* with Hop Acids

| Concentration | Tetrahydroisohumulone Growth in TSB at pH 7.0 | Hexahydrocolupulone Growth in TSB at pH 7.0 |
|---|---|---|
| 100 ppm | No growth | No growth |
| 50 ppm | No growth | No growth |
| 25 ppm | No growth | No growth |
| 12.5 ppm | No growth | No growth |
| 6.25 ppm | No growth | No growth |
| 3.125 ppm | No growth | No growth |
| 1.6 ppm | ++++ growth | No growth |
| 0.8 ppm | ++++ growth | No growth |
| 0.4 ppm | ++++ growth | No growth |
| 0.2 ppm | ++++ growth | No growth |
| 0.1 ppm | ++++ growth | No growth |
| 0.05 ppm | ++++ growth | No growth |
| 0.025 ppm | ++++ growth | ++ growth |
| 0 ppm Control | ++++ growth | ++++ growth |

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

INDUSTRIAL APPLICABILITY

The invention provides an antimicrobial agent including hop acids which inhibits the growth of acid-resistant and heat-resistant bacteria such as *Alicyclobacillus acidoterrestris* and *Alicyclobacillus acidocaldarius* in a medium.

What is claimed is:

1. A method for retarding spoilage of a fruit juice, the method comprising: adding a safe and effective amount of a hexahydrocolupulone to the fruit juice to retard spoilage of the fruit juice, wherein the fruit juice includes *Alicyclobacillus*.

2. The method of claim 1, wherein the fruit juice includes *Alicyclobacillus acidoterrestris* and/or *Alicyclobacillus acidocaldarius*.

3. The method of claim 1, wherein the tetrahydroisohumulone is present in the fruit juice in an amount of 0.05 ppm or greater.

4. The method of claim 1, wherein the fruit juice is selected from the group consisting of apple, orange, pineapple, cherry, grape, grapefruit, lemon, melon, strawberry, cherry, lemon-lime, mango, papaya, cranapple, fruit punch, peach, guava, tangerine, apricot, cranberry, and mixtures thereof.

5. The method of claim 1, wherein the fruit juice is apple juice.

* * * * *